US006860932B2

United States Patent
Oshida

(10) Patent No.: US 6,860,932 B2
(45) Date of Patent: Mar. 1, 2005

(54) DENTAL AND MEDICAL CEMENT

(76) Inventor: Yoshiki Oshida, 310 Haddonfield Dr., DeWitt, NY (US) 13214

(*) Notice: Subject to any disclaimer, the term of this patent is extended or adjusted under 35 U.S.C. 154(b) by 0 days.

(21) Appl. No.: 10/241,697

(22) Filed: Sep. 12, 2002

(65) Prior Publication Data

US 2004/0050296 A1 Mar. 18, 2004

(51) Int. Cl.$^7$ .................................................. A61K 6/06
(52) U.S. Cl. ........................ 106/35; 523/116; 623/23.62
(58) Field of Search ............................ 106/35; 523/116; 623/23.62

(56) References Cited

U.S. PATENT DOCUMENTS

| | | | |
|---|---|---|---|
| 3,814,717 A | * 6/1974 | Wilson et al. ............ 433/228.1 |
| RE33,100 E | * 10/1989 | Ibsen et al. .................... 106/35 |
| 5,141,560 A | 8/1992 | Combe et al. |
| 5,179,135 A | 1/1993 | Ellis et al. |
| 5,273,574 A | * 12/1993 | Arnold ........................ 106/35 |
| 5,369,142 A | 11/1994 | Culbertson et al. |
| 5,593,303 A | 1/1997 | Cohen et al. |
| 5,753,765 A | 5/1998 | Thomsen |
| 6,017,982 A | 1/2000 | Akinmade |
| 6,043,296 A | 3/2000 | Davies et al. |
| 6,107,229 A | 8/2000 | Lück et al. |
| 6,312,473 B1 | 11/2001 | Oshida |
| 6,342,203 B2 | 1/2002 | Warford, III et al. |

OTHER PUBLICATIONS

Richard J. Simonsen; Glass Ionomer As Fissure Sealant–A Critical Review; Journal of Public Health Denistry, 1996; vol. 56, No. 3, Special Issue 1996; pp. 146–149.

John Charnley; Arthroplasty Of The Hip–A New Operation; The Lancet, May 27, 1961, pp. 1129–1132.

Brian F. Kavanaugh and Robert H. Fitzgerald, Jr.; Multiple Revisions For Failed Total Hip Arthoplasty Not Associated With Infection; The Journal Of Bone And Joint Surgery, Incorporated; vol. 69–A, No. 8, Oct. 1987, pp. 1144–1149.

I. M. Brook and P. V. Hatton; Biomaterials, vol. 19, No. 19, pp. 565–571, 1998.

* cited by examiner

Primary Examiner—C. Melissa Koslow
(74) Attorney, Agent, or Firm—Breiner & Breiner, L.L.C.

(57) ABSTRACT

Cement materials useful in dental and medical fields with improved mechanical properties is described. The cement material includes fluoroaluminosilicate powder and poly (acrylic acid) liquid. Biocompatible oxide powders are further included resulting in improved mechanical properties of maximum strength, rigidity and toughness. Variations of the cement material resulting in improved mechanical properties include the concentration of poly(acrylic acid) liquid, and combining the fluoroaluminosilicate powder with different biocompatible oxide powders. Useful oxide powders include hydroxyapatite powders, titanium oxide, zirconium oxide, aluminum oxide, and silica-containing e-glass powder. Preferably, about 10 vol. % of total amount of oxide powders is used to obtain optimum improvements. The total amount can be based on incorporation of a single or a combination of selected oxide powders. Titanium oxide and aluminum oxide improve toughness; titanium oxide also increases strength, and zirconium oxide enhances rigidity.

6 Claims, No Drawings

DENTAL AND MEDICAL CEMENT

FIELD OF INVENTION

The present invention relates to a cement material which can be effectively used in both dental and medical fields. Specifically, the present invention directly relates to cement material which is used as a restorative material in dentistry and bone cement material in medical orthopedic applications.

BACKGROUND OF THE INVENTION

Dental caries is a disease with several signs ranging from microscopic loss of inorganic crystalline (known as a hydroxyapatite), which is invisible to the human eye, to obvious cavitation. Dental caries is the result of demineralization (selective dissolving of Ca and P ions from said hydroxyapatite crystallines) of tooth enamel, dentin, or cementum initiated by an acid produced by oral bacteria. Over time, overt cavitation will occur unless the demineralized areas are remineralized (redeposition of Ca and P ions). Hence, caries is a bacterial disease and the treatment thereof should therefore primarily revolve around overcoming the infection. Today, there is a growing consensus that different types of carious lesions exist and that the management of the disease should depend on the severity of the carious lesion as well as the caries risk status of a patient.

In recent times the term "minimal intervention dentistry" has been coined to describe a new approach to the restoration of caries lesions. As mentioned previously, caries is a bacterial disease, so that treatment should revolve primarily around overcoming the infection. It is often possible to interrupt the process and actually heal the early lesions prior to cavitation of the surface of the crown of a tooth. If this action is too late or unsuccessful, and the enamel surface is damaged sufficiently to retain plaque, then some degree of surgical intervention will become necessary to restore the smooth surface once more. But it is suggested that any surgical intervention should be as minimally invasive as possible and should provide only for the removal of completely demineralized infected tooth structure. Remaining structure, particularly demineralized or caries-affected enamel and dentin, should be retained and remineralized wherever possible. This will lead to an extensive preservation of natural tooth structure and this, in turn, will minimize aesthetic problems and at least slow down the need for replacement dentistry.

The pattern of attack of a carious lesion and its progress through the enamel and dentin has been understood for many years, and has tended to dictate the treatment methods used. However, the purely surgical approach to caries control is now recognized as being far too destructive to be used as the first line of defense. It is relatively inefficient because it does not cure the disease, and the major problem is that it leads to a continuous process of replacement dentistry wherein the cavity just gets larger and the tooth gets weaker.

The greatest value lies in the restoration of a minimal new lesion so that its biological activities can be used to the maximum and it will not be exposed to undue occlusal load. The relatively low fracture strength may be regarded as a limitation but wear resistance improves considerably as the restoration matures. This means that as long as the restoration is well surrounded by sound tooth structure it can be placed on the occlusal surface with safety. However, if the proposed restoration is to be heavily loaded then a lamination technique will need to be utilized.

Different types of restorative materials and luting cements are currently used in daily dental practice. The most common are amalgam, composite resins, glass ionomers, dental casting alloys, and ceramics. Each material possesses advantages and disadvantages. Amalgam has a long history as a practical and relatively inexpensive restorative material and is still widely used. However, the toxicity controversy of the mercury is a disadvantage. Dental casting alloys have excellent physical properties, but the production process is costly and some components of the alloy may include allergic reactions in patients, such as the nickel element. Moreover, amalgam and casting alloys are not tooth colored and the demand for more aesthetic materials is increasing. Resin composites are the most aesthetically acceptable of the available restorative materials with satisfactory physical properties. However, allergic problems have arisen and some concern about the estrogenic effects of bisphenol A as an environmental hormone has been indicated. The glass ionomer cements are more aesthetically pleasing than metallic restoratives, although less so than resin composites, and are considered one of the safest restorative materials.

Glass ionomer cements have remained an important class of dental restorative materials for almost 30 years. In this role, their attributes include adhesion to untreated tooth mineral and the release of fluoride ions that are thought to confer resistance against dental caries.

Glass ionomer cements are probably more accurately and scientifically known as glass-polyalkenoate cements. They are a true acid-base material, where the base is an inorganic fluoroaluminosilicate glass with a high fluoride content and this interacts with an organic poly(alkenoate acid). Right after the mixing of these components, calcium polyacrylate chains from aluminum ions will begin to form aluminum polyacrylate chains to produce the polyacid matrix (salts) and these are less soluble and notably stronger. The final matrix formation then takes place. The use of glass ionomer materials in dentistry has expanded tremendously. In the past 20 years clinicians have accepted glass ionomer cements as a routine part of their operative dentistry armamentarium. During the same time period attempts were made to use glass ionomer materials, both restorative cements and more diluted materials, as sealants (R. Simonsen, *J. Public Health Dent*. 1996; 56:146–149).

Now moving to the medical area which is relevant to the present application, techniques pioneered by Charnley were introduced in the 1960s for the treatment of joint dysfunction utilizing poly(methyl methacrylate) (PMMA) for cementing prosthetic hips (J. Charnley, *Lancet*, 1961; 1:129–132). The use of PMMA has enabled the successful rehabilitation of many elderly patients with a relatively short life expectancy. However, the inherent polymerization and the presence of methacrylate monomer, is a major factor in the loosening and subsequent failure of hip prostheses (B. F. Kavanagh and R. H. Fitzgerald, *J. Bone Joint Surg.* 1989; 69A:1144–1149). Despite improvements in bone cement with the introduction of systems based on poly(ethyl methacrylate) and n-butyl methacrylate monomer an ideal bone cement has not yet been produced. For improvements of mechanical strengths of PMMA materials, U.S. Pat. No. 6,312,473 B1 (issued to Y. Oshida, Nov. 6, 2001) discloses that an appropriate amount of metallic oxide powder incorporated with pre-polymerized PMMA beads and polymerizing the mixture with monomer liquid results in increasing mechanical strengths and decreasing undesired temperature rise which might be harmful to living soft tissue.

Development of glass ionomer cements for medical use has, however, fulfilled a clinical need. In otologic and reconstructive surgery increasingly sophisticated surgical techniques require methods of stabilizing implanted devices, bony fragments and reconstruction obliteration of bony defects.

The biological properties of a glass ionomer cement result from its surface chemistry, physical structure and bulk composition. Set glass ionomer cement are essentially hybrid glass polymer composites consisting of inorganic glass particles in an insoluble hydrogel matrix held together by a combination of ionic cross-links, hydrogen bridges and chain entanglements. Setting glass ionomer cements occurs by gelation of the cement with a transfer of ions from the glass to the acidic matrix. In contrast to acrylic cements, this setting reaction does not generate heat and so will not cause thermal damage to tissues at the implant site, or affect heat-labile drugs incorporated into the matrix phase of the glass ionomer cements. Unset glass ionomer cement is able to chemically bond to both bone (apatite) and metals, and during gelation does not undergo appreciative shrinkage. Glass ionomer cement, if used as a bone cement for stabilization of prosthetic implants, would not have to rely exclusively on a mechanical bond to achieve fixation.

Although mechanically inferior to acrylic cements, recent developments suggest that the physical properties of glass ionomer cements can be improved. Glass ionomer cements are, however, ideal for non-weight bearing applications where the ability exists to biomechanically match the glass ionomer cement to the bone. This can be done by varying the volume fraction of the glass and polymer components of the cement (I. M. Brook and P. V. Hatton, *Biomaterilas*, 1998; 19:565–571).

The clinical success of implanted biomaterials for tissue replacement is dependent upon the formation of a stable bone-implant interface. A pre-requisite for formation of this interface is believed to be the ability of the surface of the material to bind certain biological molecules and attract bone cells. The surface of set glass ionomer cement is hydrophilic, and a more detailed analysis of the surface using X-ray photoelectron spectroscopy shows that it is predominantly organic with trace inorganic species.

It is desirable in implanted materials, where the aim is to establish osseointegration, that the material is able to bind factors that mediate the recruitment and regulation of osteogenic cells. Immunohistochemical studies of implanted glass ionomer cements have shown close association of the non-collagenous extracellular matrix proteins of bone (osteopontin, fibronectin, and tenascin) with the glass ionomer cement surface. These factors, that are known to play an important role in osteogenesis and the osseointegration of biomaterials together with the hydrophilic surface of glass ionomer cement, may explain the osteoconductive properties of implanted glass ionomer cements.

Unlike PMMA bone cement (release of toxic monomer) or ceramic bone substitutes (relatively inert) the main effect that the bulk composition of glass ionomer cement has on their bioactivity is as a reservoir for ion release.

For orthopedic use, the advantages of glass ionomer cement over acrylic-based cements lie in the lack of exotherm during setting, absence of monomer and potential for improved release of incorporated therapeutic agents. The strength of glass ionomer cements as compared to acrylic cements, is a disadvantage in weight-bearing situations. However, the adhesive properties of glass ionomer cements may mitigate this disadvantage. Glass ionomer cements compare favorably with current acrylic-based bone cements in in vitro and in vivo tests, especially when it is remembered that they are in a far earlier stage of development.

Glass ionomer cements are not inert materials but are "bioactive". Following implantation, an appropriate host response is produced, mediated by the ion exchange, that is composition, site and tissue dependent. Glass ionomer cements can be designed as biocompatible bone substitutes and cements with osteoconductive activity eliciting a favorable biological response and clinical outcome. However, inappropriate use of glass ionomer cements, as with any substance applied to a biological system, can lead to adverse effects. Correct application and surgical technique are essential in order to produce a positive health gain.

U.S. Pat. No. 6,312,473 B1, mentioned above, also discloses that mechanical properties of the cement materials described therein can be improved by incorporating one or more metallic oxide powders in the cement materials.

OBJECTS AND SUMMARY OF THE INVENTION

In view of the foregoing, it is an object of the present invention to provide improvements in mechanical properties of glass ionomer cement materials.

Cement materials useful in dental and medical applications having improved properties is provided. The cement material of the invention includes a fluoroaluminosilicate powder and a poly(acrylic acid) liquid. The poly(acrylic acid) is preferably present in a concentration ranging from about 18% to 27%, more preferably about 25%. The mechanical properties (i.e., strength, rigidity and toughness) of the cement material are improved by the inclusion of one or more biocompatible oxide powders in the cement material. The one or more oxide powders can be incorporated directly with the fluoroaluminosilicate powder or can be added as a separate component with the other components of the cement material. Suitable biocompatible oxide powders for inclusion in the cement material include synthetic or natural hydroxyapatite powders, titanium oxide, zirconium oxide, aluminum oxide and silica-containing e-glass powder. The oxide powder(s) included in the cement material preferably have a particle size in a range of from about 50–100 $\mu$m. The oxide powder(s) is (are) incorporated in the cement material in an amount of from about 7 vol. % to 12 vol. %, more preferably about 10 vol. %.

Further improvement to the mechanical properties of the cement material is also achieved by pre-treating the biocompatible oxide powder(s) utilized with a metal primer liquid.

DETAILED DESCRIPTION OF PRESENTLY PREFERRED EMBODIMENTS

Factors relevant in relation to the cement material of the invention and the effect on mechanical properties thereof, i.e., strength, rigidity and toughness, are (1) the concentration of poly(acrylic acid) aqueous solution, (2) the type of oxide powder, (3) the particle size of the powder, (4) the volume fraction of the addition amount of oxide powder, (5) the incorporation of one or more oxide powders, (6) the application of a metal primer liquid, and (7) the pre-treatment of oxide powder with a metal primer liquid.

To show the effect of each aforementioned factor alone and in combination, samples for mechanical tests were fabricated using Teflon split molds to cast samples with dimensions of 27 mm long, 2 mm wide and 2 mm deep. Each sample was set in a three-point bending flexure supporting jig and tested under 0.75 mm/min crosshead speed. The span between two supporting points was 11.5 mm. Since the glass ionomer material is hydrophilic in nature and easily deteriorated by absorbed water/moisture, all six sides of the fabricated samples were coated with cocoa butter prior to mechanical evaluations.

Results obtained from the mechanical tests are with respect to three important properties, i.e., (a) maximum strength (in MPa unit) to breakage, (b) elastic modulus, which is a straight elastic portion of entire stress-strain curve, representing the rigidity (in GPa unit), and (c) the integrated entire area under the stress-strain curve, indicating the toughness (in N-mm unit) of the sample.

As to the effects of concentration of poly(acrylic acid) aqueous solution on mechanical properties, two sample groups were prepared. One group was fabricated using 30% concentration of poly(acrylic acid) liquid, such as used in commercially available capsules. The other group was produced using 25% concentration of poly(acrylic acid) liquid. It was found that 25% acid liquid provided better mechanical properties than those fabricated using 30% acid liquid. It was also very hard to mix powder and liquid evenly with 30% or greater concentration of poly(acrylic acid) liquid, which has much higher viscosity.

Various oxide powders were found to affect the mechanical properties of the cement materials, including certain metallic oxide powders such as synthetic hydroxyapatite (HA), bovine bone originated hydroxyapatite (BB), titanium oxide (TO), zirconium oxide (ZO), aluminum oxide (AO), and silica-containing e-glass powder (SO). Each of these oxide powders are recognized as having biocompatability with living tissue. AO and SO in fact also are main constituents in glass ionomer powder, which is basically fluoroalumino-silicate. Certain single oxide powders improve a specific mechanical property and select combinations of oxide powders serve to effect all three mechanical properties of strength, rigidity and toughness. For example, (1) titanium oxide (TO) and aluminum oxide (AO) improve strength, (2) zirconium oxide (ZO) enhances rigidity (or elastic modulus), and (3) synthetic hydroxyapatite (HA), titanium oxide (TO) and aluminum oxide (AO) increase toughness (energy-to-break). Dual addition of two types of oxide powders provide increased benefit by affecting a combination of properties.

Normally, it is believed that the finer the particle size of a powder, the more a powder can be condensed. In composite industries, mixing powders can be also done by hybridization which involves different particle sizes. In the following tests, two particle size groups were fabricated, one is the −100 μm (meaning all powders less than 100 μm diameter) group and the other is the −50 μm group. Results showed that there was no significant differences between the two particle size groups.

The addition amount of the oxide powders was found to be one of the most important parameters in providing optimum conditions. Determining the appropriate amount is based on several characteristics, not just one. The setting time was utilized as a secondary item to optimize the conditions. Oxide powders preferably are present in an amount above 5 vol. % and below 15 vol. %. About 7 vol. % to 12 vol. % is preferred, with about 10 vol. % being most preferred. Mechanical properties are not improved at 5 vol. % addition or below. By 15 vol. % addition, some oxides did not mix evenly and other oxides caused undesired prolonged setting, which is not practical.

With regard to mixing one or more oxide powders, for example the admixture of TO and AO, to glass ionomer fluoroaluminosilicate powders, the total additive amount is preferably within 10 vol. %. Thus, a powder mixture was prepared with 5 vol. % TO and 5 vol. % AO. TO addition was to improve the strength and AO addition was for increasing toughness. Accordingly, both strength and toughness are increased based on this type of combination.

Further treatment of the powder is also beneficial. A metal primer liquid is normally used in restorative dentistry for enhancing the bond strength between less-noble metal surfaces and organic substances. Surfaces of less-noble metals are normally covered with its oxide films. By applying a small amount of (for example, about one drop or 1 ml) of a metal primer to the fluoroaluminosilicate powder, and then kneading the treated powder with poly(acrylic acid) liquid, both strength and toughness were improved.

Further, pre-treatment of the additive oxide powder (for example, titanium oxide) was also found to enhance mechanical properties. An appropriate amount of oxide powder, i.e., titanium oxide powder, is pre-treated with a small amount (e.g. one drop or 1 ml) of a metal primer liquid and the treated powder then naturally dried. The thus pretreated oxide powder is then mixed with fluoroaluminosilicate and poly(acrylic acid) liquid. Both strength and toughness are improved, particularly the toughness is improved to a level near double that of a value for a control, i.e., untreated material.

Further specific embodiments and tests conducted in relation thereto are set forth below.

(1) Effects of Concentration of Poly(Acrylic Acid) Aqueous Solution on Mechanical Properties.

In order to evaluate mechanical properties of a control as well as variously treated glass ionomer cement materials, a rectangular sample (27 mm×2 mm×2 mm) was fabricated. The samples were subjected to 3-point bending flexural testing under a crosshead speed of 0.75 mm/min. Prior to mechanical tests, all sides of a sample were coated with cocoa butter to avoid dehydration and kept for 1 week at 37° C. incubator.

A commercially available delivery system of the glass ionomer cement material is normally formed as a capsule, which has a partition separating a powder component and poly acid liquid component. Upon applying, the thin film partition is broken and the powder and liquid components are mechanically mixed (usually recommended is the use of a triturating machine), followed by squeezing the mixture out of the tip of a nozzle. For the present invention, this conventional procedure is not desirable. In order to mix the fluoroaluminosilicate powder portion with oxide powders, it is required to isolate the powder only from the capsule. The mixing of the powder with the liquid is preferably done manually. The poly(acrylic acid) liquid for a conventional type of glass ionomer cement system (for example, GC Fuji IX) is normally 35±5% concentration. It was found that it was very difficult to manually mix isolated powder with 35±5% poly(acrylic acid) liquid. Even with 30%, it was also hard to mix the powder and liquid. However, it was found that it is manually mixable if 25% concentration poly(acrylic acid) liquid is used. This concentration of 25% has not only the advantage of easy handling, but it has also the beneficial effect of improving the mechanical properties as shown in the following table.

|  | Strength Peak Stress (MPa) | Rigidity Elastic Modulus (GPa) | Toughness Energy-to-Break (N-mm) |
| --- | --- | --- | --- |
| 35% poly acid | 17.20 (±4.21) | 3.305 (±0.585) | 0.18 (±0.02) |
| 30% poly acid | 12.67 (±4.89) | 4.702 (±1.167) | 0.09 (±0.08) |
| 25% poly acid | 21.31 (±4.39) | 3.913 (±1.334) | 0.32 (±0.11) |

Powder/Liquid (P/L) ratio was maintained at approximately 0.5 g/0.5 ml. If the P/L ratio is greater than 0.5 g/0.5 ml, it will become very hard to mix the powder and liquid uniformly. If the P/L ratio is less than 0.5 g/0.5 ml, it will become soupy, causing the setting time to be prolonged. Accordingly, the P/L ratio is preferably about 0.5 g/0.5 ml. Further, the P/L ratio should be kept at about the same ratio even when the powder is solely the glass ionomer inorganic powder without additives or is admixed glass ionomer powder.

(2) Effects of Different Types of Oxide Powder on Mechanical Properties.

To show the different effects of different types of oxide powder on improvements to mechanical properties, the following compositions were prepared: 25% poly acid unadmixed glass ionomer cement serving as a control, and six oxide powders admixed at 10 volume percentage. The oxide powers were HA (synthetic hydroxyapatite), BB (bovine bone originated hydroxyapatite), TO (titanium oxide), ZO zirconium oxide), AO (aluminum oxide), and SO (silica-containing e-glass powder).

|  | Strength Peak Stress (MPa) | Rigidity Elastic Modulus (GPa) | Toughness Energy-to-Break (N-mm) |
| --- | --- | --- | --- |
| 25% poly acid, Control | 21.31 (4.39) | 3.913 (1.334) | 0.32 (0.11) |
| 10 vol. % HA | 17.97 (3.99) | 2.517 (1.431) | 0.33 (0.16) |
| 10 vol. % BB | 13.96 (3.22) | 2.810 (1.157) | 0.14 (0.11) |
| 10 vol. % TO | 24.78 (5.76) | 3.75 (1.241) | 0.44 (0.21) |
| 10 vol. % ZO | 12.36 (2.81) | 4.38 (1.06) | 0.24 (0.17) |
| 10 vol. % AO | 19.31 (5.19) | 3.17 (1.58) | 0.87 (0.17) |
| 10 vol. % SO | 21.68 (3.74) | 2.93 (0.59) | 0.24 (0.10) |

From the above table, it can be seen that certain oxide powders improved select mechanical properties. For example, (1) titanium oxide (TO), aluminum oxide (AO) and silicon oxide (SO) improved strength, (2) zirconium oxide (ZO) enhanced rigidity (or elastic modulus), and (3) synthetic hydroxyapatite (HA), titanium oxide (TO) and aluminum oxide (AO) increased toughness (energy-to-break). Thus to affect all mechanical properties of strength, rigidity and toughness, a combination of certain oxide powders is selected.

(3) Effects of Particle Size on Mechanical Properties.

As to the effect of particle size, two groups were compared, i.e., the 100 $\mu$m group and 50 $\mu$m group. The 100 $\mu$m group was prepared including all powders which were smaller than 100 $\mu$m (i.e., −100 m) and the 50 $\mu$m group consisted of −50 $\mu$m powder.

|  | Strength Peak Stress (MPa) | Rigidity Elastic Modulus (GPa) | Toughness Energy-to-Break (N-mm) |
| --- | --- | --- | --- |
| Control, 100 $\mu$m | 21.31 (4.39) | 3.913 (1.334) | 0.32 (0.11) |
| Control, 50 $\mu$m | 21.18 (4.28) | 3.791 (0.780) | 0.33 (0.11) |
| 10 vol. % HA, 100 $\mu$m | 17.97 (3.99) | 2.517 (1.431) | 0.33 (0.16) |
| 10 vol. % HA, 50 $\mu$m | 19.45 (3.18) | 2.390 (0.370) | 0.39 (0.11) |

It was found that there were no significant differences between 100 $\mu$m particle size and 50 $\mu$m particle size.

(4) Effects of Volume Fraction of Addition Amount of Oxide Powder on Mechanical Properties.

To determine the appropriate range of addition amount of oxide powders, HA and TO powders were used and 5 vol. % added samples were fabricated and the mechanical properties thereof were compared with those with 10 vol. %. The comparison is shown in the following table.

|  | Strength Peak Stress (MPa) | Rigidity Elastic Modulus (GPa) | Toughness Energy-to-Break (N-mm) |
| --- | --- | --- | --- |
| 10 vol. % HA | 17.97 (3.39) | 2.517 (1.431) | 0.33 (0.16) |
| 5 vol. % HA | 14.38 (2.54) | 2.170 (0.570) | 0.16 (0.13) |
| 10 vol. % TO | 24.78 (5.76) | 3.751 (1.241) | 0.44 (0.21) |
| 5 vol. % TO | 18.90 (2.58) | 2.190 (0.240) | 0.30 (0.12) |

The 10 volume percentage is shown to be an optimal addition amount. However, less than 10 vol. % is shown to result in no remarkable improvements in mechanical properties. Greater than 10 vol. % is shown to result in a prolonged setting time and would not be practical.

(5) Effects of Single and Dual Mixing of Oxide Powder on Mechanical Properties.

As mentioned previously, certain types of oxide powder possess unique additive function(s) for improvement of mechanical properties of glass ionomer cement materials. In this test, titanium oxide (TO) and aluminum oxide (AO) were co-admixed to glass ionomer powder and their mechanical properties compared to those obtained from un-mixed control samples.

|  | Strength Peak Stress (MPa) | Rigidity Elastic Modulus (GPa) | Toughness Energy-to-Break (N-mm) |
| --- | --- | --- | --- |
| Control | 21.31 (4.39) | 3.913 (1.334) | 0.32 (0.11) |
| 5 vol. % HA + 5 vol. % TO | 23.38 (2.32) | 3.350 (0.674) | 0.69 (0.23) |

The results in the above table show that beneficial effects of both types of oxide powders can be realized. The main reason why strength and toughness did not improve to the maximum level of individual effect of each type of oxide powder is based on each powder being added at 5 vol. %, not 10 vol. %. Because of the setting limitation, it is hard and not practical to use any admixture of total 20 vol. % of oxide powders.

(6) Effects of Metal Primer Liquid on Mechanical Properties.

In restorative dentistry, a metal primer is normally applied to enhance the bond strength between a metallic (particularly less-noble metals) surface and organic substances. Radicals containing sulfur and phosphorous react with both materials to result in strong adhesion. Surfaces of less-noble metals are normally covered with its oxide film. Accordingly, the interfacial reaction of the metal primer is metal oxide and organic substances.

Among many types of metal primer commercially available, the GC METALPRIMER II was used. The addition amount was only 1 drop which is approximately 1 ml.

The following table compares without (control) and with application of the metal primer liquid.

|  | Strength Peak Stress (MPa) | Rigidity Elastic Modulus (GPa) | Toughness Energy-to-Break (N-mm) |
|---|---|---|---|
| Control | 21.31 (4.39) | 3.913 (1.334) | 0.32 (0.11) |
| 10 vol. % TO + 1 ml MP | 24.25 (3.35) | 3.712 (0.716) | 0.35 (0.08) |

It was found that strength and toughness were improved by applying a metal primer.

(7) Effects of Pre-Treatment of Oxide Powder with Metal Primer Liquid on Mechanical Properties.

The way to apply the metal primer can be done in other ways than as done in the above tests. This test was conducted to see the effects of pre-treatment of additives with a metal primer prior to fabrication of samples. Titanium oxide (which is 10 vol. % of the total sample volume) was mixed with about 1 ml of metal primer liquid and the mixture was evenly mixed and naturally dried. Later on, samples were fabricated through exactly the same procedures as done previously. The resulting mechanical properties were compared with those obtained from control samples.

|  | Strength Peak Stress (MPa) | Rigidity Elastic Modulus (GPa) | Toughness Energy-to-Break (N-mm) |
|---|---|---|---|
| Control | 21.31 (4.39) | 3.913 (1.334) | 0.32 (0.11) |
| Pre-treated 10 vol. % TO with 1 ml MP | 23.25 (2.31) | 3.537 (0.546) | 0.55 (0.07) |

As the above table indicates, pre-treatment of titanium oxide powders enhanced remarkably toughness without changing other mechanical properties.

As will be apparent to one skilled in the art, various modifications can be made within the scope of the aforesaid description. Such modifications being within the ability of one skilled in the art form a part of the present invention and are embraced by the appended claims.

What is claimed is:

1. A cement material for dental and medical application comprising fluoroaluminosilicate powder, poly(acrylic acid) liquid, and one or more biocompatible oxide powders, wherein the biocompatible oxide powders have a particle size within a range of from about 50 to 100 $\mu$m.

2. The cement material according to claim 1, wherein the one or more biocompatible oxide powders is a synthetic or natural hydroxyapatite powder produced from bovine bone, titanium oxide, zirconium oxide, aluminum oxide, and/or silica-containing e-glass powder, and wherein the one or more biocompatible oxide powders are pre-treated with a metal primer liquid.

3. A cement material for dental and medical application comprising fluoroaluminosilicate powder, poly(acrylic acid) liquid, and one or more biocompatible oxide powders, wherein the one or more biocompatible oxide powders is a synthetic or natural hydroxyapatite powder produced from bovine bone, titanium oxide, zirconium oxide, aluminum oxide, and/or silica-containing e-glass powder, and wherein the one or more biocompatible oxide powders are pre-treated with a metal primer liquid.

4. The cement material according to claim 3, wherein one or more of the biocompatible oxide powders are incorporated with the fluoroaluminosilicate powder.

5. The cement material according to claim 4, wherein the one or more biocompatible oxide powders are incorporated in an amount in a range of from above 5 vol. % to about 12 vol. %.

6. The cement material according to claim 5, wherein the amount is about 7 vol. % to about 12 vol. %.

* * * * *